United States Patent [19]
de Almeida Cunha

[11] Patent Number: 5,792,161
[45] Date of Patent: Aug. 11, 1998

[54] DEVICE AND METHOD FOR IMPLANTING AN INTRALAMELLAR RING IN THE CORRECTION OF AMETROPIAS

[76] Inventor: Paulo Ferrara de Almeida Cunha, Rua Alagoas, 1314, sala 715 Savassi, Belo Horizonte, MG, Brazil

[21] Appl. No.: 666,358
[22] PCT Filed: Oct. 27, 1994
[86] PCT No.: PCT/BR94/00036
§ 371 Date: Jun. 21, 1996
§ 102(e) Date: Jun. 21, 1996
[87] PCT Pub. No.: WO95/17144
PCT Pub. Date: Jun. 29, 1995

[30] Foreign Application Priority Data

Dec. 22, 1993 [BR] Brazil ................. 9305251

[51] Int. Cl.$^6$ ................................. A61B 17/32
[52] U.S. Cl. ............................................. 606/166
[58] Field of Search ................................... 606/166

[56] References Cited

U.S. PATENT DOCUMENTS 4,781,187 11/1988 Herrick.
5,323,788 6/1994 Silvestrini et al. ............ 128/897

FOREIGN PATENT DOCUMENTS

| A 0 557 128 | 8/1993 | European Pat. Off. |
| A 28 11 869 | 9/1979 | Germany. |
| A 36 42 521 | 6/1988 | Germany. |
| A 39 36 811 | 9/1990 | Germany. |
| A 88/10096 | 12/1988 | WIPO. |
| A 93 12735 | 7/1993 | WIPO. |
| A 93 20763 | 10/1993 | WIPO. |
| 94/06381 | 3/1994 | WIPO. |

OTHER PUBLICATIONS

Database WPI, Week 9345, Derwent Publications, Ltd., London, GB, AN 93-358291 & SU, A, 1 771 730 (Alma-Ata Doctors Training Inst.).

Database WPI; Section P.Q.; Week 9151; Dewent Publications Ltd., London, GB, Class P, AN 91-375417/51 & SU, A, 1 641 326 (Rost. Med. Inst.).

Primary Examiner—Michael H. Thaler
Attorney, Agent, or Firm—Beveridge, DeGrandi, Weilacher, & Young, LLP

[57] ABSTRACT

A device that permits and facilitates implantation of an intracorneal ring for the correction of ametropias has two semicircular complementary strip-like cutting members, a support for maintaining the cutting members in fixed relationship, and a hand held operating member which is associated with the support and has a peripheral circular finger-engaging surface. In use, two small incisions are made in the cornea and a surgeon, holding the operating member, presses the cutting members against the cornea, directing the leading ends of the cutting members into the incisions. The device is rotated 180° to create a 360° tunnel in the cornea, and then it is reversed and removed. An intralamellar split ring is introduced into the tunnel. The ring is formed of silicon or the like; and, it has apertures to facilitate manipulation during the operation, a triangular cross section, and rounded ends.

9 Claims, 3 Drawing Sheets

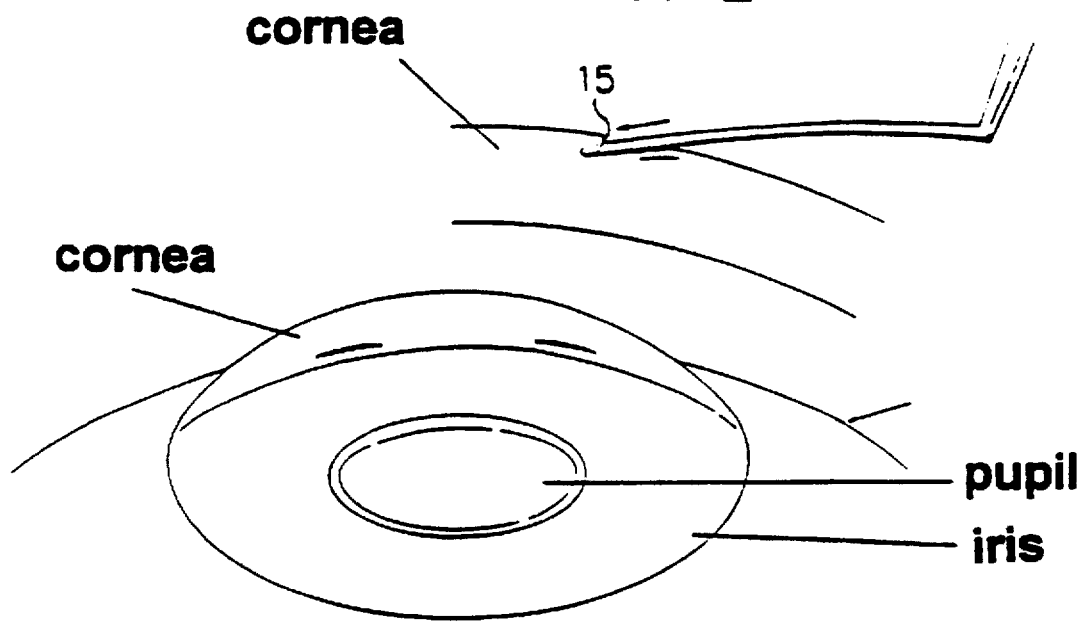
FIG. 2
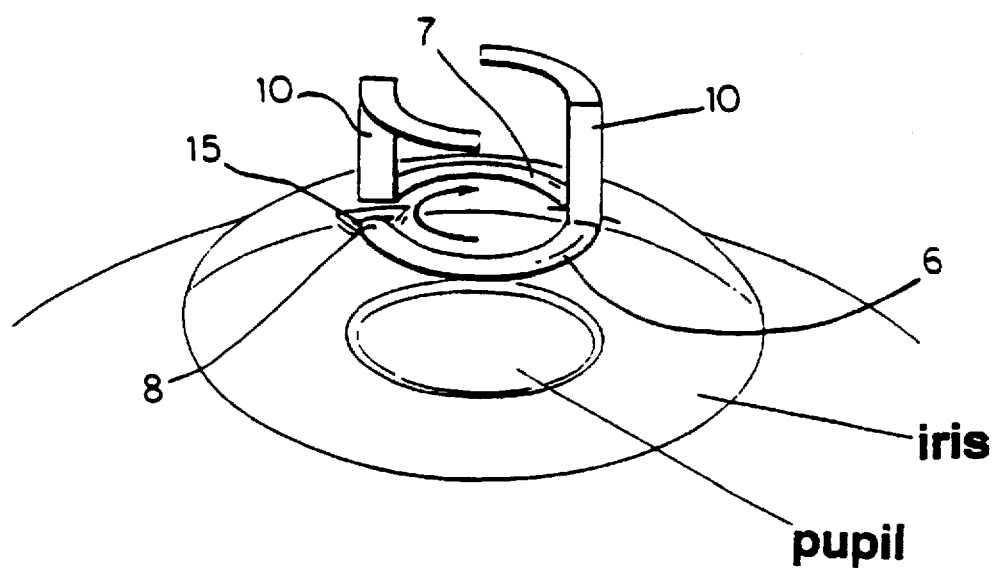
FIG. 3
FIG. 4

DEVICE AND METHOD FOR IMPLANTING AN INTRALAMELLAR RING IN THE CORRECTION OF AMETROPIAS

FIELD OF THE INVENTION AND PRIOR ART

The present invention refers to a tunnel forming device and method for permitting the implantation of an intralamellar ring in the cornea for the correction of ametropias.

The conception of an intracorneal ring has been developed by various authors. Published papers indicate, as one of the main difficulties, an easy and reliable technique for implanting the ring.

"Prior art teachings on the subject of implantation of intralamellar rings include WO-A-9320763 which teaches the use of a single cutting blade to form an incision into which an intralamellar ring may be inserted, and WO-A8810096 which teaches the use of a device for inserting an intralamellar ring in the cornea, in which the ring itself is used to form the incision. Both of the devices described in these patents require the use of complicated positioning equipment."

The techniques known so far are the "pocket discision" and the "lamellar keratectomy" by means of microkeratome. Both techniques, however, have a serious drawback, namely the interface formed at the level of the optical zone, which is detrimental to the transparency and the final visual result. Besides, the microkeratome is an expensive apparatus and requires a high degree of training, thus discouraging most surgeons from using it, especially bearing in mind the cost-benefit relationship.

SUMMARY OF THE INVENTION

The device of the present patent application overcomes these problems, enabling the intracorneal ring to be implanted very easily, besides not causing any corneal alteration. This result is achieved by forming a "tunnel" in the cornea, for implanting the ring, using a symmetrically balanced cutting arrangement.

According to the present invention a device for permitting the implantation of an intralamellar ring in the cornea for the correction of ametropias, comprises:

first and second complementary substantially semi-circular strip-like cutting members, each of the cutting members having a free leading end and a supported trailing end to define a circular annular configuration with the leading end of the first cutting member adjacent but spaced from the trailing end of the second cutting member and the leading end of the second cutting member adjacent but spaced from the trailing end of the first cutting member;

rigid cutting member support means supporting the trailing ends of the cutting members at diametrically opposite points with respect to the circular configuration; and manual operating means associated with the support means and having a peripheral circular finger engaging surface of a diameter greater than that of the circular configuration defined by the cutting members.

The use of a device of this nature in which the tunnel forming cutting members are semicircular results in balanced resistance to rotation which permits the elimination of more complicated positioning equipment as is known in the prior art. In one embodiment of this invention, the device defined above also includes a separate base member having an annular peripheral portion supporting a radially inner guide portion defining an inner diameter substantially equal to the outer diameter of the circular configuration defined by the cutting members. Placement of the base member against the cornea permits it to be used to guide the cutting members during the tunnel forming operation.

In spite of the above, however, the device of the invention has proved to be so simple to use that the base member has been found to be unnecessary. In the preferred embodiment of the invention, therefore, the rigid support means comprise a rigid outer ring and first and second L-shaped support elements, each said element having an axially directed leg having its free end fixed to the trailing edge of a respective cutting member and a radially directed leg having its free end fixed to the rigid ring. Preferably, the manual operating means comprises a tubular part arranged to be coaxial with the rigid outer ring, the ring being mountable over one end of the tubular part.

The device can be manufactured from any rigid, metallic or non-metallic material. Titanium is the preferred material.

In accordance with another aspect of the invention, a method of implanting an interlamellar ring in the cornea for the correction of ametropias, comprises the steps of:

a) effecting a pair of small radially oriented 10 incisions in the cornea at two diametrically opposite locations with respect to the axis of the iris;

b) providing a tunnel forming device having two complementary substantially semicircular cutting members in rigid fixed relation with respect to each other, each having a leading end and a trailing end, the leading end of each cutting member being circumferentially spaced from, but adjacent to the trailing end of the other cutting member;

c) placing the device over the cornea with the leading end of each of the cutting members in a respective one of the incisions;

d) pressuring the device against the cornea and twisting it through 180° in a first direction so that the leading ends form respective semicircular tunnels in the cornea;

e) twisting the device through 180° in a second opposite direction and then removing it, whereby the cornea is formed with a circular tunnel having two diametrically opposite entrances through the pair of incisions;

f) introducing a leading end of an interlamellar ring through one of the incisions and forcing it through the tunnel until it completely fills the tunnel throughout its full extension of 360°.

The interlamellar ring comprises a still further aspect of the invention and is in the form of an extension of a transparent substantially rigid material with a substantially triangular cross section, curved to form a split ring having ends closely adjacent to each other without overlap, at least one of said ends being rounded and provided with a transverse through orifice.

BRIEF DESCRIPTION OF THE DRAWINGS

The present invention will be better understood from the following description given merely by way of example, reference being made to the accompanying drawings in which:

FIG. 2 illustrates the formation of a small radially directed incision in the cornea;

FIG. 3 is a top view of the cornea with a pair of small radially oriented incisions in diametrically opposite locations with respect to the axis of the iris, prior to a tunnel forming operation;

FIG. 4 shows the device of FIG. 1 being applied to the cornea to form a tunnel of 360°;

DETAILED DESCRIPTION OF THE PREFERRED EMBODIMENTS

Figure 1:
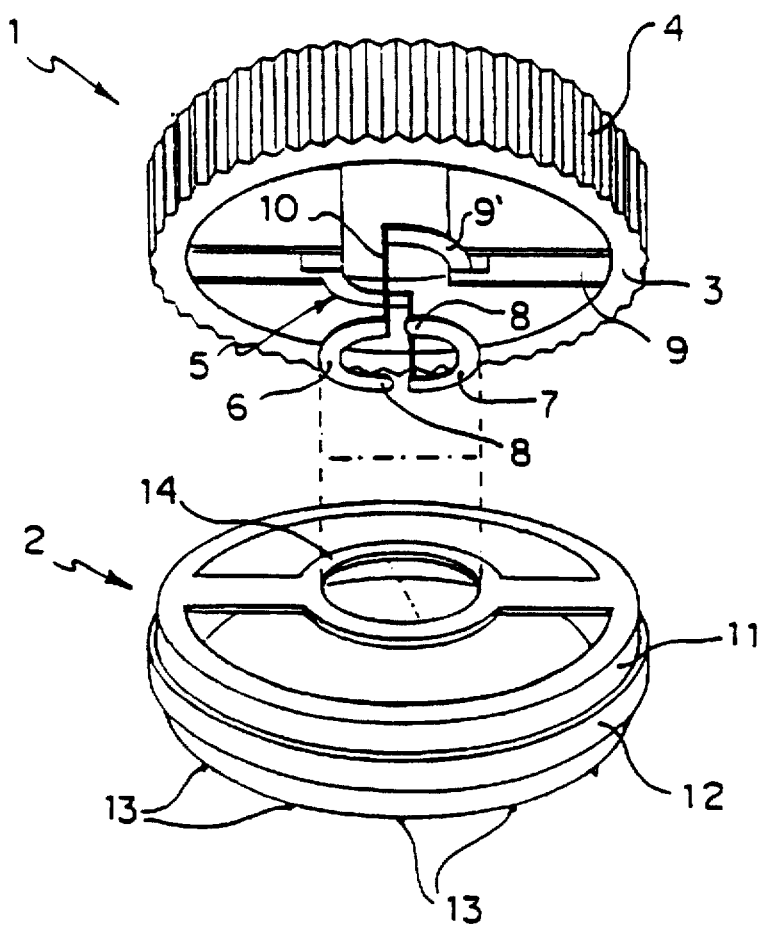
FIG. 1 is a perspective view of a tunnel forming device according to a first embodiment of the invention.
Figure 5:
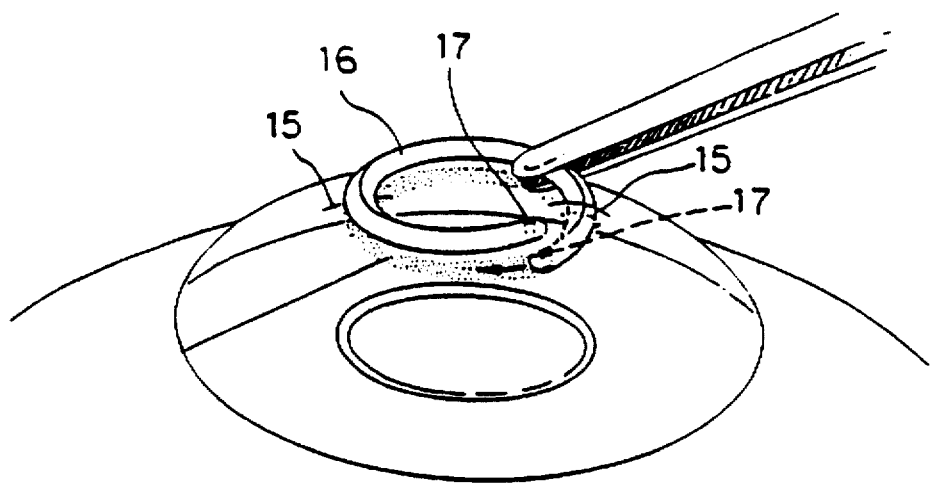
FIG. 5 shows the introduction of an intralamellar ring into a tunnel formed in the cornea by the device illustrated in FIG. 1.

FIG. 1 is a perspective view of a first embodiment of a tunnel forming device for permitting the implantation of an intralamellar ring in the cornea for the correction of ametropias. The device illustrated comprises an upper operating part 1 and a lower base or guide part 2.

The operating part 1 comprises a rigid hand held ring 3 with a knurled circular outer surface region 4 for manipulation by the fingers of the surgeon. Internally, the ring is provided with a pair of supports 5 for a pair of tunnel forming cutting members 6 and 7, the supports 5 being joined to the ring 3 at diametrically opposite points. The cutting members 6 and 7 are strip-like blade members of semicircular shape, each having a trailing end attached to one of the supports and a free leading end 8. The leading ends are sharpened in their thickness and rounded in their width. It will be observed that each leading end 8 is circumferentially closely paced from the trailing end of the other of the cutting members, without any overlap. Consequently, the cutting members 6 and 7 define a circular annular configuration.

It will also be noted that each support 5 comprises a first radial strut 9 having fixed thereto an arcuate part 9' substantially in the plane of the ring 3 and, integral with the latter an axially directed part 10 to which is that is connected the trailing edge of the respective cutting member 6 or 7. It is to be noted that parts 10 are parallel to and not coincident with the axis of ring 3. As a consequence, the annular tunnel formimg combination comprising the cutting members 6 and 7 lies in a plane parallel to that of ring 3 but, in FIG. 1, projected a small distance below the ring.

The lower base part 2 comprises a second ring 11 having an outer annular projection 12 to facilitate handling using forceps or the like. Its axially lower (in FIG. 1) end is formed with a series of small axially directed teeth 13 so that, on being pressed downwardly, it will grip against the cornea without risk of rotation. Internally ring 11 supports a ring shaped guide portion 14 having an inner surface with a diameter substantially equal to that of the outer diameter of the annular configuration defined by cutting members 6 and 7.

FIGS. 2 and 3 illustrate how a pair of small radially oriented incisions 15 may be made in the cornea, at diametrically opposite locations with respect to the axis of the iris, using the leading ends of cutting member 6 or 7.

It will be readily understood from FIG. 4 in conjunction with the description given with respect to FIG. 1, that when base part 2 is pressed against the cornea, the operating part 1 can be fitted over base part 2 with the cutting members guided in guide portion 14. The surgeon will then place the sharpened leading ends 8 of the cutting members in the respective incisions 15, apply a firm pressure to the operating part 1 and then rotate it slowly through 180° whereby the cutting members cut respective 180° tunnels in the cornea. On completion of this movement, the rotation (180°) is reversed and the device removed. At this time there is a complete (360°) circular tunnel in the cornea with two diametrically opposite entrances (the incisions 15). The surgeon then selects in a pair of forceps a suitable intralamellar ring 16 such as that illustrated in FIG. 6 and inserts it into one of the incisions 15. He then forces it through the tunnel until it virtually completes the 360°. If it proves difficult by pushing with the forceps for the front end of intralamellar ring 16 to reach the end of the tunnel, it may be reached from the other end, the forceps engaging in the transverse orifice 17 so that the ring may then be pulled to the desired position.

It should be noted that the intralamellar ring 16 is of a triangular cross section, that the ends are rounded to assist entry through the incision 15 and that each end is provided with a transverse orifice 16. Ring 17 may be made of any suitable, preferably transparent material that should be sufficiently rigid to be inserted in the tunnel formed by the device of this invention. Preferably it comprises acrylic or silicon but it may also be made of other inert materials.

Figure 6:
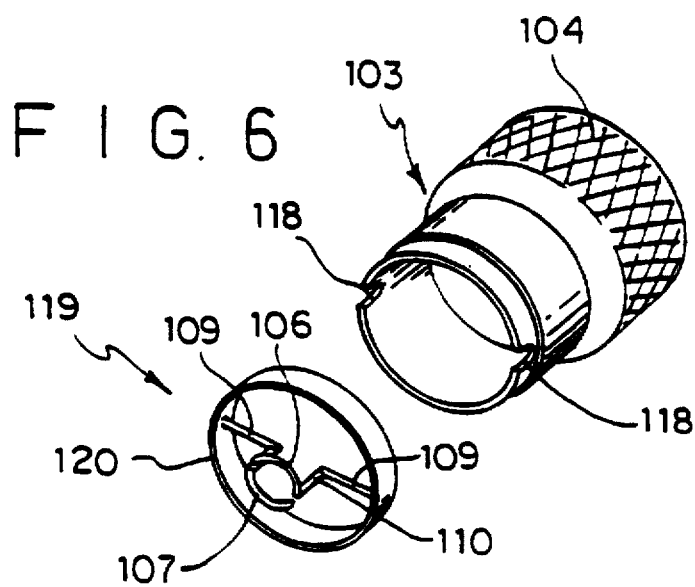
FIG. 6 is a perspective view of a second and presently preferred embodiment of a tunnel forming device according to the present invention.

FIG. 6 shows a second, but presently preferred embodiment of the present invention in the form of a tunnel forming device in which there is no lower base part 2 as is illustrated in FIG. 1 with respect to the first embodiment. It has been found that by increasing the axial dimension of the operating part so as to facilitate handling by the surgeon, the base or guide part is no longer necessary and in fact its absence facilitates the operation as there is one less part to be positioned correctly and removed at the end. In the case of the FIG. 6 embodiment the cutting members 106 and 107 are identical to members 6 and 7 in the first embodiment and they will therefore not be further described.

The operating device 101 of FIG. 6 comprises a tubular hand held member 103 having a knurled circular outer surface portion 104 for manipulation by the fingers of the surgeon. It is to be observed that the surface part 104 is at the top end of the tubular member 103 which extends further down to a lower end where there are diametrically opposite slots 118. In practice, tubular member 103 has a length of about 2 cm and a diameter of about 2 cm in the region of the knurled surface portion 104 which has an axial extension of about 1 cm. The end of member 103 opposite that of the knurled surface is of a reduced diameter of about 1.1 cm.

The device 101 of FIG. 6 also comprises a rigid cutter part 119 in the form of a rigid outer ring 120 having an inner diameter substantially the same as the outer diameter of the lower end of tubular member 103 on which the ring is to be received by means of an interference fit. Ring 119 is also provided with a pair of L-shaped support 105. Each first leg 109 is radially inwardly directed, the two legs 109 lying along a diameter of ring 120. The second leg 110 of each support 115 is axially directed and supports at its lower end the trailing end of its respective cutting member 106 or 107.

When ring 120 is fitted over the lower end of tubular member 103, the outer ends of legs 109 are accommodated by the slots 118 in the lower end of the tubular member.

In use, device 101 is of great simplicity although it creates a tunnel in the cornea in a manner identical to that of the FIG. 1 embodiment. Having first made the two incisions 15 in the cornea, the cutter part 119 is fitted over the tubular member 103 and the surgeon holds the latter between his fingers, introduces the leading ends of cutter members 106 and 107 in the incisions 15 and pressing the device against the cornea rotates the device, exactly as in the first embodiment but without the presence of the base part 2.

The cutting members of the two embodiments have dimensions suitably within the following ranges:

Outer diameter: 3.00 to 12.00 mm

Inner diameter: 2.00 to 11.00 mm

Width of the strip: 0.50 to 2.00 mm

Thickness: 0.10 to 0.30 mm

The hand held member and the cutter part may be made of metallic or non-metallic material. Silver and gold may be used, but the cutting members in particular should be of a relative hardness and titanium is the preferred. material. It is to be noted that in both embodiments, the use of two symmetrically arranged cutting members makes it extremely easy to produce a circular tunnel in the cornea since the resistance to rotation of the cutter is perfectly balanced.

I claim:

1. Method of implanting an interlamellar ring in the cornea for the correction of ametropias, comprising the steps of:
    a) effecting a pair of small radially oriented incisions in the cornea at two diametrically opposite locations with respect to the axis of the iris;
    b) providing a tunnel forming device having two complementary substantially semicircular cutting members in rigid fixed relation with respect to each other, each having a leading end and a trailing end, the leading end of each of said cutting members being circumferentially spaced from, but adjacent to the trailing end of the other of said cutting members;
    c) placing said device over the cornea with the leading end of each of the cutting members in a respective one of said incisions;
    d) pressuring said device against the cornea and twisting it through 180° in a first direction so that said leading ends cut respective semicircular tunnels in the cornea;
    e) twisting said device through 180° in a second opposite direction and then removing said device, whereby said cornea is formed with a circular tunnel having two diametrically opposite entrances through said pair of incisions;
    f) introducing a leading end of an interlamellar ring through one of said incisions and forcing it through said tunnel until said ring completely fills said tunnel throughout its full extension of 360°.

2. A device according to claim 1, in which said manual operating means comprises an annular part (3;103) arranged to be coaxial with said circular configuration, and said support means comprise first and second supports (5,105) respectively connecting said trailing ends of said cutting members (6,7;106,107) to diametrically opposite regions of said annular part.

3. A device according to claim 2, in which each of said first and second supports (5;105) comprises a first portion (10;110) substantially parallel to the axis of said annular part and a second portion (9;109) substantially parallel to the plane defined by said cutting members.

4. A device according to claim 3, further comprising a base member (2) having annular peripheral portion (11) supporting a radially inner guide portion (14) having an inner diameter substantially equal to the outer diameter of said circular configuration.

5. A device according to claim 4, further comprising small teeth (13) distributed around an axial end edge of said annular peripheral portion (11) for preventing rotation of said base member (2) when pressed against the cornea of a patient.

6. A device according to claim 1 in which said rigid support means comprise a rigid outer ring (120) and first and second L-shaped support elements (105), each said element having an axially directed leg (110) having its free end fixed to said trailing edge of a respective said cutting member (106,107) and a radially directed leg (109) having its free end fixed to said rigid ring (120).

7. A device according to claim 6, in which said manual operating means comprises a tubular part (103) arranged to be coaxial with said rigid outer ring (119), and further including mounting means (103,118) for mounting said ring (119) on said tubular part (103).

8. Device according to claim 7, in which said mounting means include a pair of diametrically opposite radial slots (119) in an end of said tubular part (103), said end having an outer diameter substantially the same as the inner diameter of said rigid outer ring (120), said radial slots (118) being dimensioned to accommodate said radially directed legs (109) of said L-shaped support elements (105) when said ring is fitted over said end of said tubular part.

9. A device for permitting the implantation of an intralamellar ring in the cornea for the correction of ametropias, comprising cutting means having a free leading end (8) and a trailing end supported by rigid support means, said support means associated with a manual operating means, and said cutting means defining a substantially circular annular configuration, characterized in that:

said cutting means comprises first and second complementary substantially semicircular strip-like cutting members (6,7; 106, 107), with said free leading end of said first cutting member (6; 106) adjacent but spaced from said trailing end of said second cutting member (7; 107) and said free leading end of said second cutting member (7; 107) adjacent but spaced from said trailing end of said first cutting member (6; 106);

said support means (5, 105) supports said trailing ends of first and second cutting members (6, 7; 106, 107) at diametrically opposite points with respect to said circular annular configuration; and said manual operating means (3; 103) has a peripheral circular finger engaging surface (4; 104) having a diameter greater than that of said circular annular configuration defined by said cutting members (6, 7; 106, 107).

* * * * *

UNITED STATES PATENT AND TRADEMARK OFFICE
CERTIFICATE OF CORRECTION

PATENT NO. : 5,792,161
DATED : August 11, 1998
INVENTOR(S) : DE ALMEIDA CUNHA

It is certified that error appears in the above-indentified patent and that said Letters Patent is hereby corrected as shown below:

Column 1, bridging lines 8 and 9, the spelling of "intrlamellar" should be --intralamellar--.

Column 2, line 21, the spelling of "interlamellar" should be --intralamellar--; line 44, the spelling of "interlamellar" should be --intralamellar--; line 48, the spelling of "interlamellar" should be --intralamellar--.

Column 5, line 17 (claim 1, line 1), the spelling of "interlamellar" should be --intralamellar--; line 42 (claim 1, line 25), the spelling of "interlamellar" should be --intralamellar--.

Signed and Sealed this

First Day of December, 1998

*Attest:*

BRUCE LEHMAN

*Attesting Officer*     *Commissioner of Patents and Trademarks*